United States Patent
Tanaka et al.

(10) Patent No.: US 9,499,473 B2
(45) Date of Patent: Nov. 22, 2016

(54) METHOD FOR PRODUCING NITROUS ACID ESTER, AND METHOD FOR PRODUCING DIALKYL OXALATE AND DIALKYL CARBONATE

(71) Applicant: UBE INDUSTRIES, LTD., Ube-shi, Yamaguchi (JP)

(72) Inventors: Syuji Tanaka, Ube (JP); Hirofumi Il, Ube (JP); Akira Hino, Ube (JP); Yuya Fukui, Ube (JP); Satoshi Ueda, Ube (JP)

(73) Assignee: UBE Industries, Ltd., Yamaguchi (JP)

( * ) Notice: Subject to any disclaimer, the term of this patent is extended or adjusted under 35 U.S.C. 154(b) by 266 days.

(21) Appl. No.: 14/389,583

(22) PCT Filed: Feb. 27, 2013

(86) PCT No.: PCT/JP2013/055148
§ 371 (c)(1),
(2) Date: Sep. 30, 2014

(87) PCT Pub. No.: WO2013/150840
PCT Pub. Date: Oct. 10, 2013

(65) Prior Publication Data
US 2015/0065742 A1 Mar. 5, 2015

(30) Foreign Application Priority Data
Apr. 2, 2012 (JP) ................................. 2012-083711

(51) Int. Cl.
C07C 201/04 (2006.01)
C07C 68/00 (2006.01)
C07C 67/36 (2006.01)

(52) U.S. Cl.
CPC ............. *C07C 201/04* (2013.01); *C07C 67/36* (2013.01); *C07C 68/00* (2013.01)

(58) Field of Classification Search
None
See application file for complete search history.

(56) References Cited

FOREIGN PATENT DOCUMENTS

| CN | 1186801 | 7/1998 |
|----|---------|--------|
| CN | 101143821 | 3/2008 |
| JP | 6-298706 | 10/1994 |
| JP | 11-189570 | 7/1999 |
| JP | 2003-327562 | 11/2003 |
| JP | 2004-002336 | 1/2004 |
| JP | 2004-091484 | 3/2004 |
| JP | 2004-107336 | 4/2004 |
| JP | 2004-323470 | 11/2004 |

*Primary Examiner* — Rebecca Anderson
*Assistant Examiner* — Po-Chih Chen
(74) *Attorney, Agent, or Firm* — Hamre, Schumann, Mueller & Larson, P.C.

(57) ABSTRACT

A method for producing nitrous acid ester in which nitric oxide, oxygen, and an alcohol are reacted, thereby generating nitrous acid ester includes a step of generating nitrous acid ester by supplying a bottom liquid from a bottom part of the reaction column, and nitric oxide and/or carbon monoxide, a step of supplying nitrous acid ester to the reaction column; a step of supplying a reaction liquid containing water, nitric acid, and the alcohol to a nitric acid condensing column from the reactor; and a step of separating a low-boiling point component by distillation from the reaction liquid under control of a concentration of the alcohol in a condensed liquid being generated at a bottom part of the nitric acid condensing column to be less than 4.0% by weight so as to introduce the condensed liquid into the reactor from the nitric acid condensing column.

10 Claims, 5 Drawing Sheets

METHOD FOR PRODUCING NITROUS ACID ESTER, AND METHOD FOR PRODUCING DIALKYL OXALATE AND DIALKYL CARBONATE

TECHNICAL FIELD

The present invention relates to a method for producing nitrous acid ester in which nitric oxide, oxygen, and an alcohol are reacted, and a method for producing a dialkyl oxalate and a dialkyl carbonate.

BACKGROUND ART

As a method for producing nitrous acid ester in which nitric oxide, oxygen, and an alcohol are reacted, a method is known in which an alcohol is supplied to the upper part of a reaction column, is made to flow downward from the upper part to the lower part of the reaction column, nitric oxide and oxygen, or a gas mixture thereof is supplied to the lower part of the reaction column, nitric oxide, oxygen, and the alcohol are reacted so as to generate nitrous acid ester, and nitrous acid ester is extracted from the top part of the reaction column (refer to Patent Literature 1 and 2).

In addition, another method is known in which a bottom liquid is extracted from the bottom part of a reaction column, and the bottom liquid is supplied to a reactor for nitric acid conversion, and is brought into contact with carbon monoxide and nitric oxide in the reactor for nitric acid conversion, thereby generating nitrous acid ester (refer to Patent Literatures 3 and 4).

CITATION LIST

Patent Literature

[Patent Literature 1] Japanese Unexamined Patent Application Publication No. 11-189570
[Patent Literature 2] Japanese Unexamined Patent Application Publication No. 6-298706
[Patent Literature 3] Japanese Unexamined Patent Application Publication No. 2004-2336
[Patent Literature 4] Japanese Unexamined Patent Application Publication No. 2004-91484

SUMMARY OF INVENTION

Technical Problem

However, even when the method for converting nitric acid into nitrous acid ester using nitric oxide or carbon monoxide is used, a liquid waste discharged from the reactor for nitric acid conversion contains a significant amount of nitric acid. According to the present inventors' studies, it was not possible to reduce the concentration of nitric acid in the liquid waste to below a range of 1 to 2% by weight.

The invention has been made in consideration of the above-described circumstances, and an object of the invention is to provide a method for producing nitrous acid ester capable of decreasing the loss of a nitrogen component that is a raw material by further reducing the concentration of nitric acid in the liquid waste. In addition, another object of the invention is to provide a method for producing a dialkyl oxalate and a dialkyl carbonate capable of reducing the loss of the nitrogen component that is used as a raw material by applying the above-described method for producing nitrous acid ester.

Solution to Problem

As a result of intensive studies, the inventors found that, when the concentration of nitric acid in the reactor for nitric acid conversion is increased by condensing a reaction liquid of the reactor for nitric acid conversion using a nitric acid condensing column, and returning the condensed reaction liquid to the reactor for nitric acid conversion, the above-described problem can be solved.

That is, the invention has, specifically, the following configuration. The invention is a method for producing nitrous acid ester in which an alcohol is supplied to an upper part of a reaction column for producing nitrous acid ester (hereinafter, also referred to as "reaction column"), is made to flow downward from the upper part to a lower part of the reaction column, nitric oxide and oxygen, or a gas mixture thereof is supplied to the lower part of the reaction column, nitric oxide, oxygen, and the alcohol are reacted, thereby generating nitrous acid ester, the method including:

a step of extracting a bottom liquid containing water, nitric acid, and an alcohol from the bottom part of the reaction column so as to supply the bottom liquid to a reactor for nitric acid conversion (hereinafter, also referred to as "reactor"), supplying nitric oxide and/or carbon monoxide to the reactor, and generating nitrous acid ester by brining nitric oxide and/or carbon monoxide into contact with the bottom liquid in the reactor;

a step of supplying nitrous acid ester obtained in the reactor to the reaction column;

a step of supplying a reaction liquid containing water, nitric acid, and the alcohol to a nitric acid condensing column, and separating a low-boiling point component by distillation under control of a concentration of the alcohol in a condensed liquid being generated at a bottom part of the nitric acid condensing column to be less than 4.0% by weight; and a step of extracting the condensed liquid from the lower part of the nitric acid condensing column so as to introduce the condensed liquid into the reactor.

In the invention, it is preferable that the nitrous acid ester obtained in the reactor be supplied to an arbitrary height below a middle part of the reaction column. In addition, in the invention, it is preferable that the bottom liquid of the reaction column extracted from the bottom part of the reaction column be guided to and cooled in a cooler, and the cooled bottom liquid of the reaction column be circulated to the middle part of the reaction column.

In the invention, it is preferable that an inside of the nitric acid condensing column be depressurized to lower than an atmospheric pressure. The reaction liquid is preferably supplied to an upper part of the nitric acid condensing column. In addition, in the invention, it is preferable that an alcohol in the low-boiling point component separated by distillation in the nitric acid condensing column be purified and supplied to the upper part of the reaction column for producing nitrous acid ester.

In the invention, it is preferable that a bottom temperature of the nitric acid condensing column be 90° C. or lower. It is preferable that gas supplied to the reactor be carbon monoxide, and the carbon monoxide and the reaction liquid be brought into contact with each other in the reactor in the presence of a platinum group catalyst.

The invention provides a method for producing a dialkyl oxalate in which nitrous acid ester produced using the above-described method for producing nitrous acid ester and carbon monoxide are reacted in the presence of a catalyst, thereby producing a dialkyl oxalate. In addition, the invention provides a method for producing a dialkyl carbonate in which nitrous acid ester produced using the above-described method for producing nitrous acid ester and carbon monoxide are reacted in the presence of a catalyst, thereby producing a dialkyl carbonate.

Advantageous Effects of Invention

According to the invention, it is possible to sufficiently reduce the concentration of nitric acid in a liquid waste by effectively reusing a nitric acid compound being generated as a byproduct. Then, it is possible to reduce the loss of a nitrogen component that is used as a raw material.

DESCRIPTION OF EMBODIMENTS

Preferred embodiments of the invention will be described below with reference to the accompanying drawings as necessary. In the respective drawings, the same or equivalent components will be given the same reference sign, and in some cases, duplicate description will not be made. Meanwhile, the following embodiments are examples of the embodiments of the invention, and the invention is not limited to the following embodiments.

A method for producing nitrous acid ester of the present embodiment is a method for producing nitrous acid ester through a nitric acid reduction process using carbon monoxide. The method for producing nitrous acid ester can be preferably applied to a method for producing an oxalate diester and a method for producing a carbonate diester.

Figure 1:
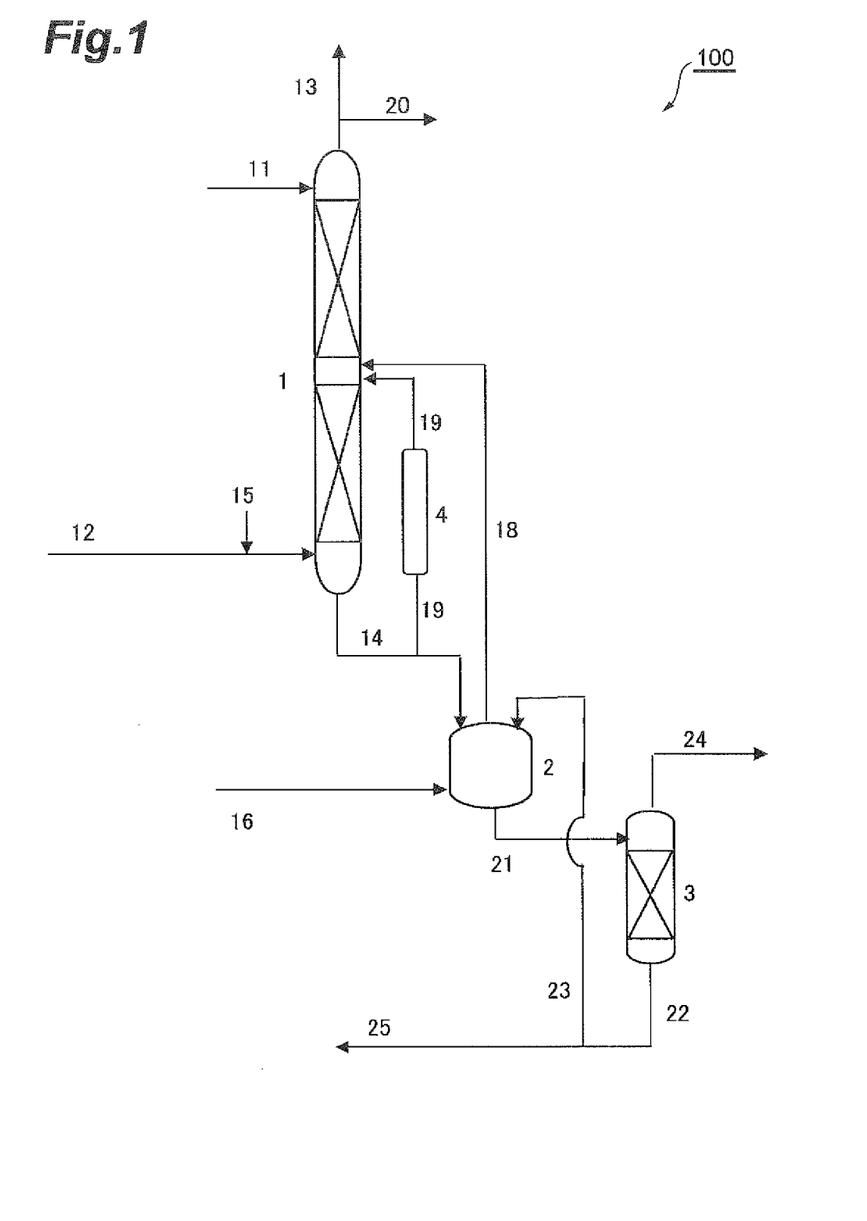
FIG. 1 is a view illustrating a schematic configuration of an apparatus for producing nitrous acid ester to which an embodiment of a method for producing nitrous acid ester of the invention is applied.

FIG. 1 is a view illustrating an apparatus for producing nitrous acid ester used to carry out the method for producing nitrous acid ester of the embodiment. In an apparatus 100 for producing nitrous acid ester in FIG. 1, a liquid-form alcohol is supplied to an upper part of a reaction column 1 for producing nitrous acid ester (hereinafter, also referred to as 'reaction column 1') from an alcohol supply line 11 (hereinafter, also referred to as 'pipe 11').

The upper part of the reaction column 1 in the present specification, refers to a part on an upper side of a middle part of the reaction column 1 in the vertical direction. The middle part of the reaction column 1 in the specification refers to a section having a height of 40 to 60 when the height of the reaction column 1 is considered to be 100. A lower part of the reaction column 1 in the specification refers to a part on a lower side of the middle part of the reaction column 1 in the vertical direction.

The upper part of the reaction column 1 is provided with a supply opening for supplying an alcohol. The pipe 11 is connected to the supply opening. The alcohol supplied to the upper part of the reaction column 1 from the supply opening through the pipe 11 is made to flow downward from the upper part of the reaction column 1.

A supply opening for supplying nitric oxide to the reaction column 1 is provided on the lower side of the middle part of the reaction column 1. A raw material gas supply line 12 (hereinafter, also referred to as 'pipe 12') is connected to the supply opening Nitric oxide that has been made to flow through the pipe 12 is supplied to the lower part of the reaction column 1 from the supply opening. The nitric oxide supplied to the lower part of the reaction column 1 flows upward from the lower part of the reaction column 1.

An oxygen supply line 15 (hereinafter, also referred to as 'pipe 15') is connected to the pipe 12. The pipe 15 may be connected to the lower part of the reaction column 1, or may be connected to both the lower part of the reaction column 1 and the pipe 12. Oxygen is supplied to the pipe 12 and/or the lower part of the reaction column 1 through the pipe 15. Among the pipe and the lower part of the reaction column, oxygen is preferably supplied to the pipe 12 in terms of the reaction efficiency. In this case, a gas mixture of nitric oxide and oxygen is supplied to the lower part of the reaction column 1.

The alcohol, the nitric oxide, and the oxygen that have been supplied to the reaction column 1 are reacted in the reaction column 1, thereby generating nitrous acid ester. Examples of the reaction at this time include a reaction expressed by the following formula (1). A first reaction gas extraction line 13 (hereinafter, also referred to as 'pipe 13') is connected to a top part of the reaction column 1. A first reaction gas containing nitrous acid ester generated through the following formula (1) or the like is obtained through extraction from the reaction column 1 using the pipe 13. Meanwhile, in the reaction column 1, a reaction expressed by the following formula (2) may develop in addition to the reaction expressed by the following formula (1). In the formulae (1) and (2), R represents an alkyl group.

$$2NO + 2ROH + \tfrac{1}{2}O_2 \rightarrow 2RONO + H_2O \quad (1)$$

$$NO + \tfrac{3}{4}O_2 + \tfrac{1}{2}H_2O \rightarrow HNO_3 \quad (2)$$

A bottom liquid in the reaction column 1 contains at least water, an unreacted alcohol, and nitric acid. The bottom liquid is extracted from the lower part of the reaction column 1 using a bottom liquid extraction line 14 (hereinafter, also referred to as 'pipe 14'), and is supplied to a reactor 2 for nitric acid conversion (hereinafter, also referred to as 'reactor 2'). The pipe 14 may be connected to a location at which the bottom liquid in the lower part of the reaction column 1 is extracted, and specifically, is preferably connected to a bottom part of the reaction column 1. The location at which the pipe 14 is connected to the reactor 2 is not particularly limited, but is preferably connected to an upper part of the rector 2 in terms of ease of the supply of the bottom liquid to the reactor 2.

The bottom liquid supplied to the reactor 2 through the pipe 14 is brought into contact with carbon monoxide and/or nitric oxide, thereby generating nitrous acid ester through, for example, reactions expressed by the formulae (3) and (4). That is, nitric acid, an alcohol, carbon monoxide, and nitric oxide are reacted, and nitrous acid ester is generated. Meanwhile, in the formulae (3) and (4), R represents an alkyl group.

$$HNO_3 + 2NO + 3ROH \rightarrow 3RONO + 2H_2O \quad (3)$$

$$HNO_3 + CO + ROH \rightarrow RONO + H_2O + CO_2 \quad (4)$$

A second reaction gas containing the nitrous acid ester generated in the reactor 2 is extracted from a second reaction gas extraction line 18 (hereinafter, also referred to as 'pipe 18'), and is supplied to the reaction column 1. The pipe 18 is connected to a supply opening that is provided on the upper side of the middle part of the reaction column 1 in the vertical direction as illustrated in FIG. 1. Therefore, the second reaction gas is supplied to the upper part of the reaction column 1.

In a case in which carbon monoxide is used as a gas that is brought into contact with the bottom liquid in the reactor 2, the bottom liquid and carbon monoxide are preferably brought into contact with each other in the presence of a catalyst in terms of the improvement of the reaction efficiency. The catalyst being used here is preferably a catalyst containing a platinum group metal, and is more preferably a catalyst containing palladium. The catalyst containing a platinum group metal is preferably a catalyst having a platinum group metal supported by a carrier. In addition, a reaction liquid in the reactor 2 is preferably controlled to be 10° C. to 60° C.

The amount of the platinum group metal supported in the above-described catalyst is preferably in a range of 0.01 to 10% by weight, and more preferably in a range of 0.2 to 2% by weight with respect to the carrier. Examples of the carrier configuring the catalyst include inert carriers such as activated carbon, alumina, silica, diatomaceous earth, pumice, zeolite, and molecular sieves. Among the above-described carriers, alumina is preferred, and α-alumina is particularly preferred.

In a case in which carbon monoxide is supplied to the reactor 2, carbon monoxide is supplied to the reactor 2 using a carbon monoxide supply line 16 (hereinafter, also referred to as 'pipe 16') as illustrated in FIG. 1. The pipe 16 is preferably connected to a lower part of the reactor 2 in terms of the reaction efficiency of carbon monoxide. That is, the pipe 16 is preferably connected to a supply opening provided on the lower side of a middle part of the reactor 2 in the vertical direction. In addition, in a case in which carbon monoxide is supplied to the reactor 2, as illustrated in FIG. 1, the pipe 18 is preferably connected to the middle part of the reaction column 1 in a height direction. Then, it is possible to reduce the oxidization of carbon monoxide in the second reaction gas.

The upper part of the reactor 2 in the specification refers to a part on an upper side of the middle part of the reactor 2 in the vertical direction. The middle part of the reactor 2 in the specification refers to a section having a height of 40 to 60 when the height of the reactor 2 is considered to be 100. A lower part of the reactor 2 in the specification refers to a part on a lower side of the middle part of the reactor 2 in the vertical direction.

The carbon monoxide supplied to the reactor 2 through the pipe 16 and carbon monoxide supplied using a second carbon monoxide supply line 32 described below may be supplied from the same carbon monoxide source, or may be supplied from different carbon monoxide sources.

Figure 2:
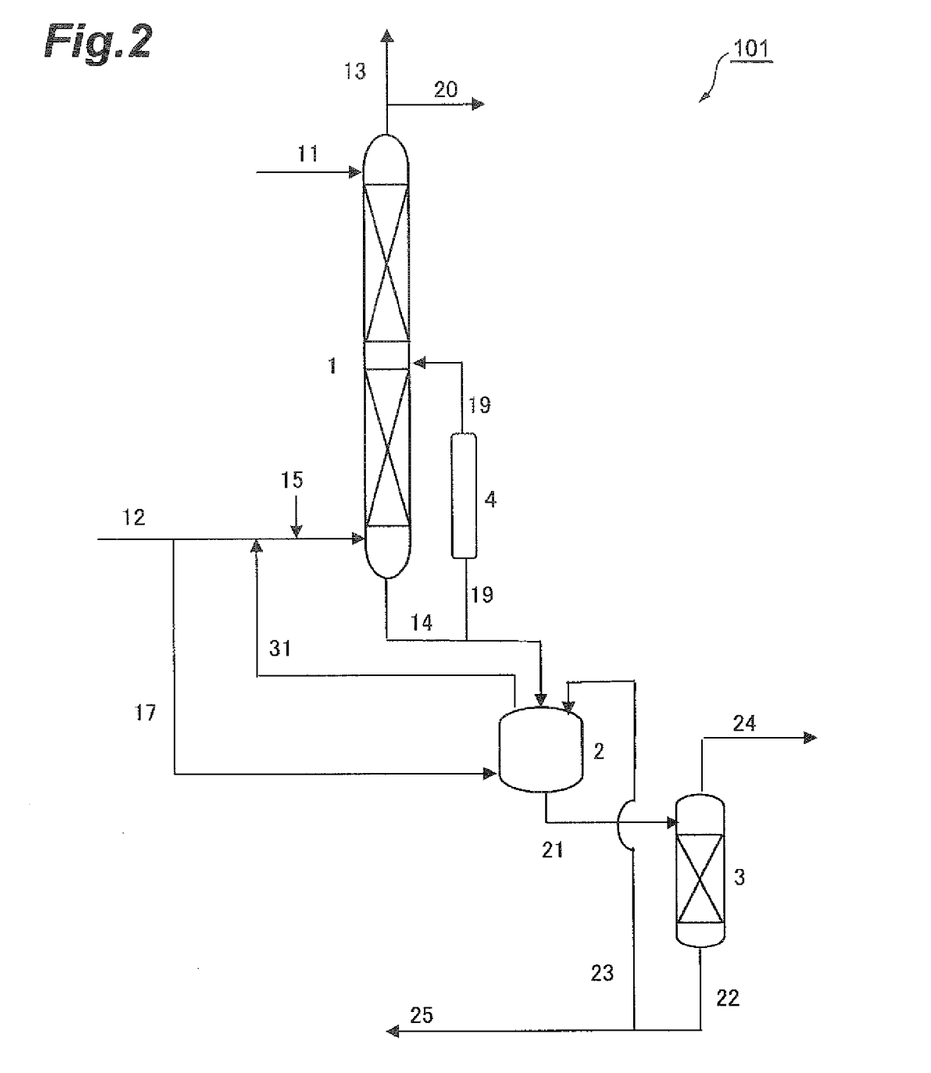
FIG. 2 is a view illustrating a schematic configuration of an apparatus for producing nitrous acid ester to which another embodiment of the method for producing nitrous acid ester of the invention is applied.
Figure 3:
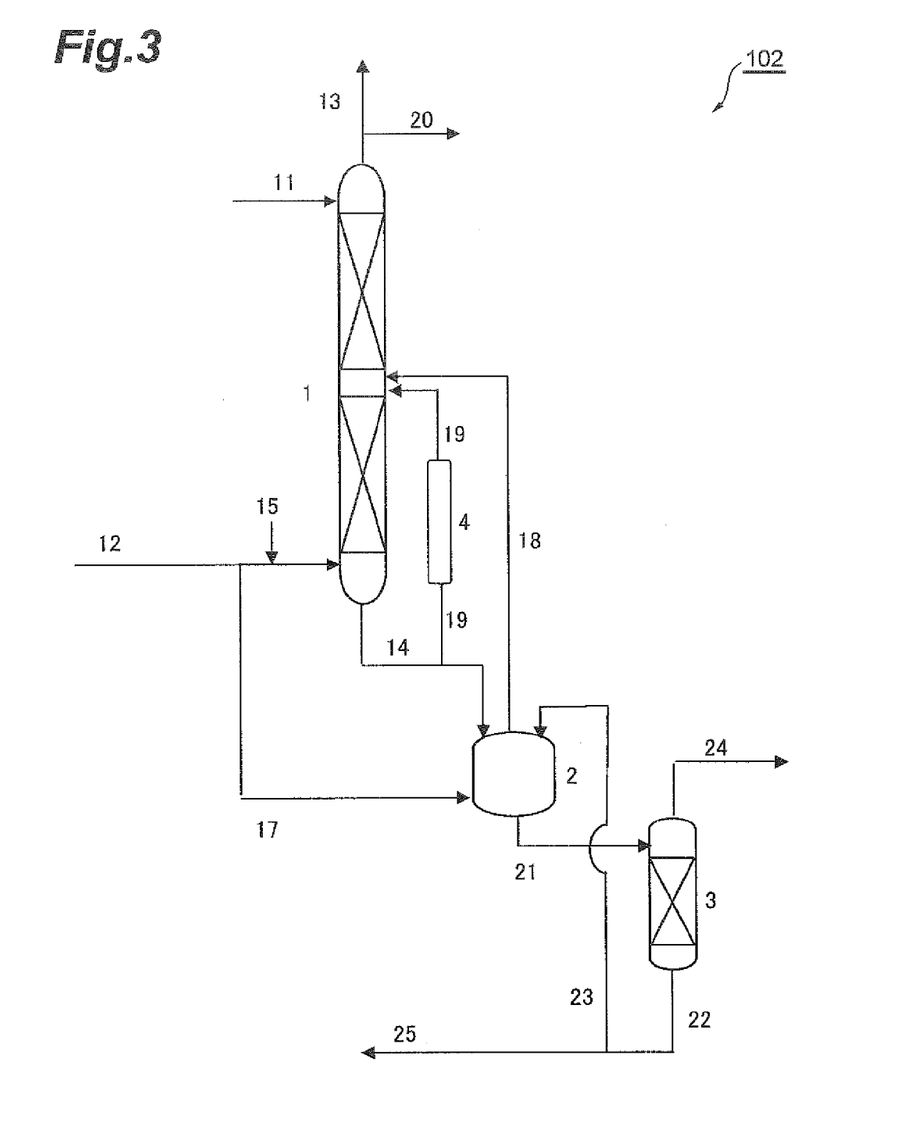
FIG. 3 is a view illustrating a schematic configuration of an apparatus for producing nitrous acid ester to which the other embodiment of the method for producing nitrous acid ester of the invention is applied.

FIG. 2 is a view illustrating another embodiment of the apparatus for producing nitrous acid ester used to carry out the method for producing nitrous acid ester. FIG. 3 is a view illustrating the other embodiment of the apparatus for producing nitrous acid ester used to carry out the method for producing nitrous acid ester. In the apparatus for producing nitrous acid ester 101 illustrated in FIG. 2 and the apparatus for producing nitrous acid ester 102 illustrated in FIG. 3, a nitric oxide supply line 17 (hereinafter, also referred to as 'pipe 17') is connected to the reactor 2. In a case in which nitric oxide is supplied to the reactor 2, the nitric oxide is supplied to the reactor 2 using the pipe 17 as illustrated in FIGS. 2 and 3. The pipe 17 is preferably connected to the lower part of the reactor 2 in terms of the reaction efficiency of nitric oxide. In addition, in a case in which nitric oxide is supplied to the reactor 2, a gas containing nitric oxide flowing through the pipe 12 may be supplied to the reactor 2 using the pipe 17 as illustrated in FIGS. 2 and 3. In addition, nitric oxide may be supplied to the reactor 2 using another pipe from a nitric oxide gas tank.

In a case in which nitric oxide is supplied to the reactor 2, it is possible to return the second reaction gas to the pipe 12 using a second reaction gas extraction line 31 (hereinafter, also referred to as 'pipe 31') as illustrated in FIG. 2. In this case, it is possible to more efficiently react nitric oxide in the second reaction gas by returning the second reaction gas to a location on an upstream side of a connection part between the pipe 15 supplying oxygen and the pipe 12.

Meanwhile, it is also possible to supply the second reaction gas to the reaction column 1 using the pipe 18 as illustrated in FIG. 3. In this case, it is possible to more efficiently generate nitrous acid ester from the second reaction gas by supplying the second reaction gas to the middle part of the reaction column 1.

In the apparatuses 100, 101 and 102 for producing nitrous acid ester, some or all of the bottom liquid extracted from the lower part of the reaction column 1 using the pipe 14 can be circulated to the reaction column 1 through a bottom liquid circulation line 19 (hereinafter, also referred to as 'pipe 19') and a cooler 4. The above-described circulation is preferably carried out in a case in which the control of the reaction temperature in the reaction column 1 is required. The reaction temperature in the reaction column 1 is preferably in a range of 0° C. to 100° C., more preferably in a range of 5° C. to 80° C., and still more preferably in a range of 10° C. to 60° C. A circulation liquid flowing through the pipe 19 is preferably supplied to the middle part of the reaction column 1.

A reaction liquid extracted from the reactor 2 using a reaction liquid extraction line 21 (hereinafter, also referred to as 'pipe 21') is supplied to a nitric acid condensing column 3. The pipe 21 may be connected to a location at which the reaction liquid in the reactor 2 is extracted. The pipe 21 is preferably connected to the lower part of the reactor 2, and is more preferably connected to the bottom part in terms of the extraction efficiency of the reaction liquid.

The pipe 21 may be connected to a location in which the reaction liquid can be supplied to the nitric acid condensing column 3. The pipe 21 is preferably connected to an upper part of the nitric acid condensing column 3 in terms of the condensing efficiency of the reaction liquid. The upper part of the nitric acid condensing column 3 in the specification refers to a part on an upper side of a middle part of the nitric acid condensing column 3 in the vertical direction. The middle part of the nitric acid condensing column 3 in the specification refers to a section having a height of 40 to 60 when the height of the reaction column 1 is considered to be 100. A lower part of the nitric acid condensing column 3 in the specification refers to a part on a lower side of the middle part of the nitric acid condensing column 3 in the vertical direction.

When the reaction liquid is supplied to the upper part of the nitric acid condensing column 3, it is possible to distill the alcohol contained in the reaction liquid until the reaction liquid reaches a bottom part of the nitric acid condensing column. Then, it becomes possible to suppress the contact of the reaction liquid with a condensed liquid having a high nitric acid concentration in a state of a high alcohol concentration, and it is possible to suppress the generation of alkyl nitrate. Since alkyl nitrate is an explosive liquid, it is preferable to reduce the amount of alkyl nitrate being accumulated during steps.

In the nitric acid condensing column 3, the reaction liquid containing at least water, the alcohol, and nitric acid is heated and condensed, and some or all of water or the alcohol that is a low-boiling point substance is distilled out as a distillate liquid. Then, it is possible to obtain a condensed liquid in which nitric acid is condensed. In the nitric acid condensing column 3, the concentration of the alcohol in the condensed liquid generated at the bottom part of the nitric acid condensing column 3 is controlled to be less than 4.0% by weight. Then, it is possible to suppress the generation of nitrous acid ester from the reaction between nitric acid and the alcohol at the bottom part of the nitric acid condensing column 3. Since nitrous acid ester is an explosive liquid, it is preferable to reduce the amount of nitrous acid ester being accumulated during steps. In the nitric acid condensing column 3, the concentration of the alcohol in the condensed liquid generated at the bottom part of the nitric acid condensing column 3 is preferably controlled to be less than 3.6% by weight.

The concentration of the alcohol in the condensed liquid generated at the bottom part of the nitric acid condensing column 3 can be controlled by adjusting the size of the nitric acid condensing column 3, the temperature and pressure at the bottom part, the number of theoretical stages, the extraction amount of the condensed liquid, and the like.

The concentration of the alcohol in the condensed liquid may be measured by, for example, sampling the condensed liquid extracted using a pipe 22, and carrying out a gas chromatography distillation test, or may be measured using an online analyzer. In a case in which an online analyzer is used, the online analyzer may also be provided with a control unit that, based on an input signal of the detection result of the concentration of the alcohol from the online analyzer, sends out an output signal adjusting the pressure of the nitric acid condensing column 3, the temperature and pressure at the bottom part, and the extraction amount of the condensed liquid. That is, it is possible to provide the control unit to, based on a signal regarding the concentration of the alcohol from the online analyzer, carry out a control treatment (for example, the control of the flow rate of the alcohol being supplied to the nitric acid condensing column 3, the control of the temperature in the nitric acid condensing column 3, the control of the cooling efficiency of the cooler 4, and the like) of changing the operation state of the nitric acid condensing column 3. When the concentration of the alcohol in the condensed liquid is automatically controlled as described above, it is possible to increase the operation efficiency.

The pressure in the nitric acid condensing column 3 is not particularly limited, but is preferably depressurized to lower than an atmospheric pressure. When the reaction liquid is condensed under depressurization, it is possible to further decrease the concentration of the alcohol in the condensed liquid. The pressure in the nitric acid condensing column 3 may be, for example, in a range of 6 kPa to 70 kPa, or in a range of 10 kPa to 50 kPa. The temperature at the bottom part in the nitric acid condensing column 3 may be, for example, in a range of 30° C. to 90° C., or in a range of 40° C. to 85° C. When the temperature at the bottom part of the nitric acid condensing column 3 is decreased, it is possible to suppress the generation of methyl nitrate.

The distillate liquid is extracted from a distillate liquid extraction line 24 (hereinafter, also referred to as 'pipe 24') connected to the upper part of the nitric acid condensing column 3. It is also possible to reuse the alcohol separated by distilling the distillate liquid extracted from the pipe 24. The alcohol being reused can be temporarily stored in a tank for the alcohol depending on necessity, and can be supplied into a reaction system from the pipe 11 connected to the upper part of the reaction column 1.

In a case in which the alcohol is reused, nitrous acid ester in the distillate liquid tends to be accumulated in the alcohol. Therefore, it is possible to reduce the amount of nitrous acid ester being accumulated in the alcohol by reducing the concentration of nitrous acid ester in the distillate liquid. When the distillate liquid is neutralized, and then distilled, thereby separating the alcohol, it is possible to further reduce the concentration of nitrous acid ester in the alcohol to be reused. The concentration of nitrous acid ester in the distillate liquid is preferably less than 50 ppm by weight, more preferably less than 30 ppm by weight, and still more preferably less than 20 ppm by weight.

The condensed liquid condensed in the nitric acid condensing column 3 is supplied to the reactor 2 using a condensed liquid extraction line 22 (hereinafter, also referred to as 'pipe 22') and a condensed liquid circulation line 23 (hereinafter, also referred to as 'pipe 23'). The pipe 22 is preferably connected to the lower part of the nitric acid condensing column 3, and is more preferably connected to a bottom part. The pipe 23 is preferably connected to the upper part of the reactor 2, and is more preferably connected to a top part. Some of the condensed liquid can be treated as a liquid waste using a liquid waste extraction line 25 (hereinafter, referred to as 'pipe 25'). Since the liquid waste of the embodiment has a sufficiently reduced concentration of nitric acid, even when being treated as a liquid waste, it is possible to sufficiently reduce a nitrogen source such as nitric oxide that is used as a raw material.

It is prefer to fill the nitric acid condensing column 3 with a packing material such as a regular packing material or an irregular packing material, and to improve the number of theoretical stages of the distillation. The number of theoretical stages of the nitric acid condensing column 3 is preferably one or more, and more preferably five or more. The number of theoretical stages of the nitric acid condensing column 3 may be, for example, in a range of 1 to 20, or may be in a range of 5 to 10.

To adjust the pressure in the reaction system, it is also possible to purge some of the reaction gas and the like outside the reaction system using a purge line 20 (hereinafter, also referred to as 'pipe 20'). In the respective embodiments, the purge line 20 is connected to the pipe 13. However, the position of the purge line is not limited to the above-described embodiments, and the purge line may be connected to any pipe as long as gas flows through the pipe.

All of the apparatuses for producing nitrous acid ester 100, 101, and 102 are provided with the nitric acid condensing column that condenses a nitric acid component by distilling a low-boiling point component from the reaction liquid coming from the reactor 2. In addition, when the concentration of the alcohol in the nitric acid condensed liquid from the nitric acid condensing column is maintained at 4 mass % or less, it is possible to sufficiently reduce the nitric acid component in alkyl nitrate or the like that is infused into the low-boiling point component. Then, it is possible to sufficiently reduce the amount of the nitric acid component that is to be treated as a liquid waste. In addition, when the nitric acid condensed liquid is circulated to the reactor 2, the nitric acid component is effectively used. Therefore, it is possible to sufficiently reduce nitric oxide that is used as a raw material.

Figure 4:
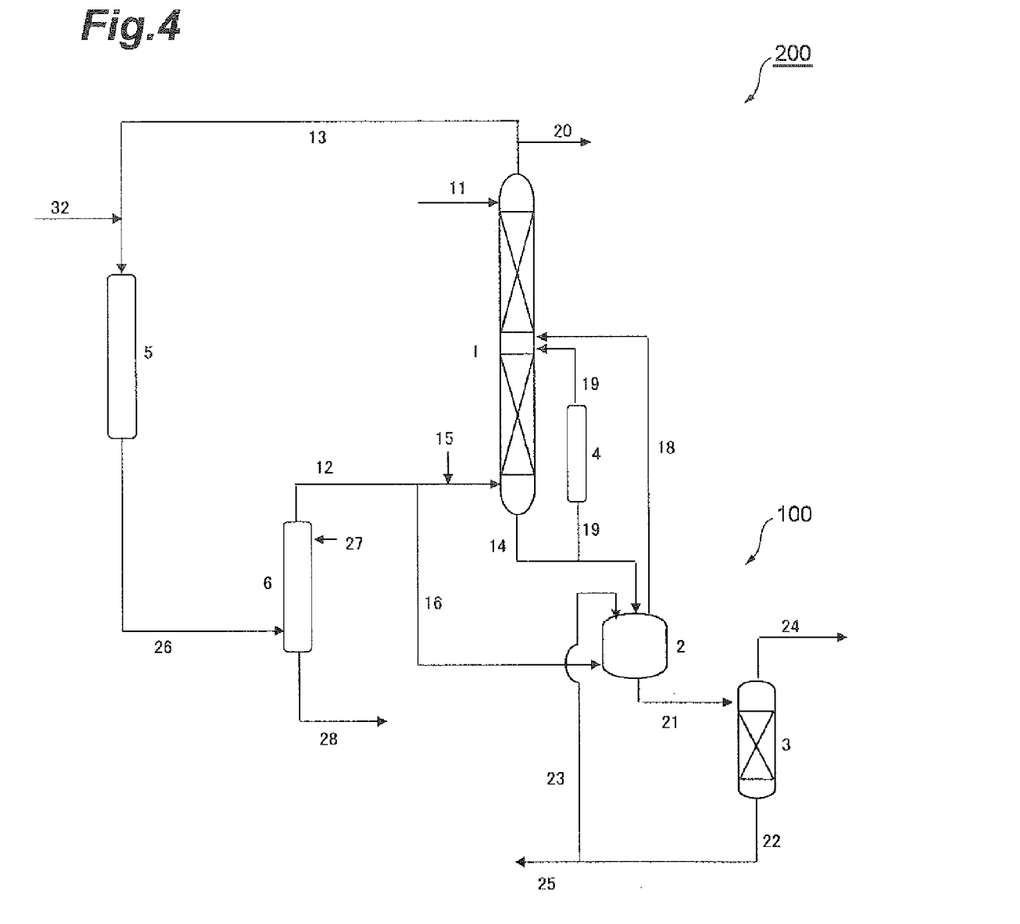
FIG. 4 is a view illustrating a schematic configuration of a producing apparatus to which an embodiment of a method for producing an oxalate diester and a method for producing a carbonate diester of the invention is applied.
Figure 5:
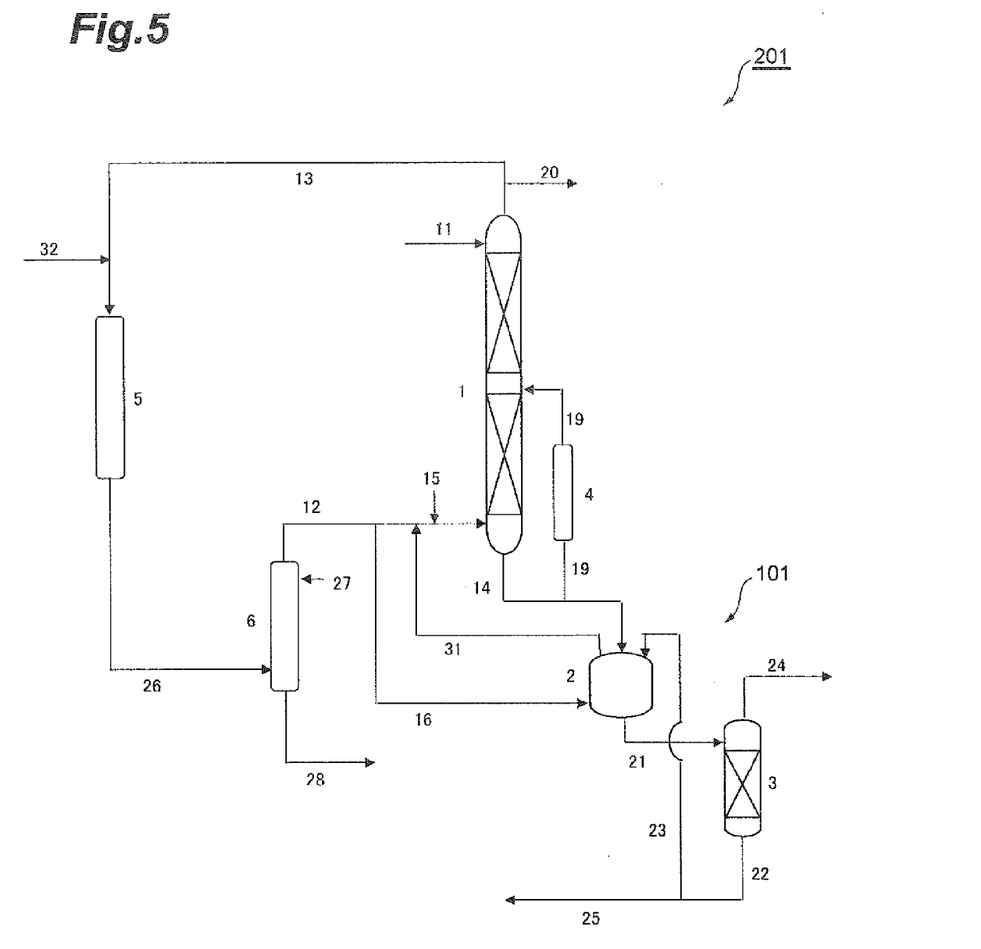
FIG. 5 is a view illustrating a schematic configuration of the producing apparatus to which another embodiment of a method for producing an oxalate diester and a method for producing a carbonate diester of the invention is applied.

FIG. 4 is a view illustrating a schematic configuration of a producing apparatus to which a method for producing an oxalate diester or a method for producing a carbonate diester of the embodiment is applied. FIG. 5 is a view illustrating a schematic configuration of a producing apparatus to which a method for producing an oxalate diester or a method for producing a carbonate diester of another embodiment is applied. An apparatus 200 for producing an oxalate diester or a carbonate diester illustrated in FIG. 4 includes the apparatus 100 for producing nitrous acid ester illustrated in FIG. 1. An apparatus 201 for producing an oxalate diester or a carbonate diester illustrated in FIG. 5 includes the apparatus 101 for producing nitrous acid ester illustrated in FIG. 2.

As illustrated in FIGS. 4 and 5, it is also possible to produce an oxalate diester and a carbonate diester using the first reaction gas containing nitrous acid ester extracted from the pipe 13. In these cases, the pipe 13 is connected to a reactor for producing an oxalate diester and/or a carbonate diester 5 (hereinafter, also referred to as 'reactor 5'). The first reaction gas is supplied to the reactor 5 (hereinafter, also referred to as 'reactor 5') through the pipe 13. On an upper side of the reactor 5, the carbon monoxide supply line 32 (hereinafter, also referred to as 'pipe 32') is connected to the pipe 13. The first reaction gas flowing through the pipe 13 is supplied to the reactor 5 together with the carbon monoxide being supplied from the pipe 32. In the reactor 5, nitrous acid ester contained in the first reaction gas and carbon monoxide are reacted as expressed by the following formulae (5) and/or (6), thereby generating an oxalate diester and/or a carbonate diester. In the formulae (5) and (6), R represents an alkyl group.

$$CO+2RONO \rightarrow ROC(=O)OR+2NO \quad (5)$$

$$2CO+2RONO \rightarrow (RCO_2)_2+2NO \quad (6)$$

The carbon monoxide being supplied using the carbon monoxide supply lines (the pipes 16 and 32) may be pure carbon monoxide, may have been diluted using an inert gas such as nitrogen, and may contain hydrogen gas or methane gas.

The reactor 5 is not particularly limited, but is preferably a single tube or multiple tube heat exchanger-type reactor. In the reactor 5, nitrous acid ester and carbon monoxide are preferably reacted in the presence of a catalyst for producing an oxalate diester and/or a catalyst for producing a carbonate diester. As the catalyst for producing an oxalate diester or the catalyst for producing a carbonate diester, a well-known catalyst such as palladium can be used, and a catalyst supported by a carrier such as alumina may also be used. Regarding the reaction temperature or pressure in the reactor 5, it is also possible to employ well-known conditions.

The oxalate diester produced using the producing method of the embodiment is preferably a dialkyl oxalate. Two alkyl groups in a dialkyl oxalate molecule may be identical or different. Examples of the dialkyl oxalate include dialkyl oxalates such as dimethyl oxalate, diethyl oxalate, dipropyl oxalate, diisopropyl oxalate, dibutyl oxalate, dipentyl oxalate, dihexyl oxalate, diheptyl oxalate, dioctyl oxalate, dinonyl oxalate, ethyl methyl oxalate, and ethyl propyl oxalate. Among dialkyl oxalates, dialkyl oxalates having a straight-chain or branched-chain alkyl group with 1 to 10 carbon atoms are preferred from the viewpoint of the reaction rate of an ester exchange reaction and ease of the removal of alkyl alcohol generated as a byproduct, and a dimethyl oxalate or a diethyl oxalate are more preferred.

The carbonate ester produced using the producing method of the embodiment is preferably a dialkyl carbonate. Two alkyl groups in a dialkyl carbonate molecule may be identical or different. Examples of the dialkyl carbonate include dialkyl carbonates such as dimethyl carbonate, diethyl carbonate, dipropyl carbonate, diisopropyl carbonate, dibutyl carbonate, dipentyl carbonate, dihexyl carbonate, diheptyl carbonate, dioctyl carbonate, dinonyl carbonate, ethyl methyl carbonate, and ethyl propyl carbonate.

Among dialkyl carbonates, dialkyl carbonates having a straight-chain or branched-chain alkyl group with 1 to 10 carbon atoms are preferred from the viewpoint of the reaction rate of an ester exchange reaction and ease of the removal of alkyl alcohol generated as a byproduct, and dimethyl carbonate or diethyl carbonate are more preferred.

A third reaction gas containing an oxalate diester and/or a carbonate diester obtained using the reactor 5 is supplied to an absorption column 6 through a third reaction gas extraction line 26 (hereinafter, also referred to as 'pipe 26'). In addition to the pipe 26, an absorption liquid supply line 27 (hereinafter, also referred to as 'pipe 27') is connected to the absorption column 6. An absorption liquid for absorbing an oxalate diester and/or a carbonate diester in the third reaction gas is supplied to the absorption column 26 from the pipe 27.

The pipe 26 is connected to a lower part of the absorption column 6, and the pipe 27 is connected to an upper part of the absorption column 6. The above-described configuration enables the improvement of the absorption efficiency of an oxalate diester and/or a carbonate diester in the absorption column 6. The absorption liquid is preferably an alcohol and/or an oxalate diester.

The oxalate diester and/or carbonate diester absorbed into the absorption liquid in the absorption column 6 is extracted from a condensate liquid extraction line 28 (hereinafter, also referred to as 'pipe 28') connected to a bottom part of the absorption column 6 together with the absorption liquid. The absorption liquid containing the oxalate diester and/or carbonate diester extracted from the absorption column 6 is purified through a purification step such as distillation. Then, an oxalate diester and/or a carbonate diester can be obtained.

Meanwhile, a gas component that is not absorbed into the absorption liquid in the absorption column 6 is supplied to the reaction column 1 as a raw material gas through the raw material gas supply line 12 connected to the upper part of the absorption column 6.

Thus far, the preferred embodiments of the invention have been described; however, needless to say, the invention is not limited to the above-described embodiments. For example, in the producing apparatuses 200 and 201, a carbonate diester and an oxalate diester may be separately produced, or a carbonate diester and an oxalate diester may be produced at the same time by adjusting the content ratio between carbon monoxide and nitrous acid ester in the first reaction gas, thereby obtaining a mixture thereof.

EXAMPLES

Hereinafter, the content of the invention will be described in more detail with reference to examples and comparative examples. However, the invention is not limited to the following examples by any means.

Example 1

A distillation process was carried out using an apparatus including the reactor 2 and the nitric acid condensing column 3 as illustrated in FIG. 1. A continuous distillation apparatus having the following configuration was used as the nitric acid condensing column 3. That is, a container made up of a spherical portion of approximately 100 ml that formed the bottom part of the nitric acid condensing column 3 and a cylindrical portion having a diameter of 25 mm and a height of 275 mm that was coupled with an opening in an upper part of the spherical portion was prepared. The spherical portion was loaded with five Sulzer labo packing EXs (product name, manufactured by Sumitomo Heavy Industries, Ltd.) as a packing material. The spherical portion of the container was provided with a configuration capable of being heated using an oil bus for heating. The pipe 21 was connected to an upper side (the upper part of the nitric acid condensing column 3) of the packing material in the cylindrical portion, and the pipe 24 was connected to an upper end, that is, a column top of the cylindrical portion. In addition, the pipe 22 was connected to a lower part of the spherical portion.

A reaction liquid having the following composition was continuously supplied from the reactor 2 to the upper part of the nitric acid condensing column 3 through the pipe 21 at a flow rate of 199.2 g/h.

The composition of the reaction liquid: 30.8% by weight of methanol, 1.6% by weight of nitric acid, 61.7% by weight of water, and 5.9% by weight of others In the nitric acid condensing column 3, the reaction liquid was heated and condensed under conditions of 300 Torr (approximately 40 kPa), a bottom part temperature of 78° C., and a column top temperature of 69° C. A distillate liquid was extracted from the column top part of the nitric acid condensing column 3 through the pipe 24 at a distillation amount of 169.4 g/h. A condensed liquid was extracted from the bottom part of the nitric acid condensing column 3 through the pipe 22 at an extraction amount of 29.8 g/h.

At this time, the compositions of the distillate liquid and the condensed liquid were as described below. The concentration of methyl nitrate in the distillate liquid was 0.2 ppm by weight. The compositions of the distillate liquid and the condensed liquid were analyzed using a gas chromatography distillation test.

The composition of the distillate liquid: 36.2% by weight of methanol, 57.6% by weight of water, and 6.2% by weight of others The composition of the condensed liquid: 0.006% by weight of methanol, 10.7% by weight of nitric acid, 85.0% by weight of water, and a remainder of others (approximately 4.3% by weight)

The results of Example 1 are summarized in Table 1. In Example 1, it was possible to sufficiently reduce the concentration of methyl nitrate in the distillate liquid. That is, in Example 1, it becomes possible to reuse a nitrate compound (methyl nitrate) contained in a liquid waste of the related art by circulating the nitrate compound to the reactor 2. Therefore, it became possible to effectively use a nitrogen component being supplied into the apparatus.

Example 2

A distillation process was carried out in the same manner as in Example 1 except for the facts that the flow rate of the reaction liquid supplied to the nitric acid condensing column 3 from the reactor 2 was set to 200.1 g/h, and the extraction amount of the condensed liquid from the nitric acid condensing column 3 was set to 17.8 g/h. The results of Example 2 are summarized in Table 1.

The temperature at the bottom part of the nitric acid condensing column 3 was 80° C., and the compositions of the distillate liquid and the condensed liquid were as described below. The concentration of methyl nitrate in the distillate liquid was 0.6 ppm by weight.

The composition of the distillate liquid: 33.8% by weight of methanol, 60.1% by weight of water, and 6.1% by weight of others The composition of the condensed liquid: 0.105% by weight of methanol, 18.0% by weight of nitric acid, 78.0% by weight of water, and a remainder of others (approximately 3.9% by weight)

Example 3

A distillation process was carried out in the same manner as in Example 1 except for the facts that the number of the Sulzer labo packing EXs loaded into the cylindrical portion of the nitric acid condensing column 3 was set to one, the flow rate of the reaction liquid supplied to the nitric acid condensing column 3 from the reactor 2 was set to 199.8 g/h, and the extraction amount of the condensed liquid from the nitric acid condensing column 3 was set to 17.8 g/h. The results of Example 3 are summarized in Table 1.

The temperature at the bottom part of the nitric acid condensing column 3 was 81° C., and the compositions of the distillate liquid and the condensed liquid were as described below. The concentration of methyl nitrate in the distillate liquid was 8 ppm by weight.

The composition of the distillate liquid: 33.7% by weight of methanol, 60.3% by weight of water, and 6.0% by weight of others The composition of the condensed liquid: 0.9% by weight of methanol, 18.0% by weight of nitric acid, 76.0% by weight of water, and 5.1% by weight of others

Example 4

The pipe 21 was connected to a changed location of the lower part of the nitric acid condensing column 3 from the upper part of the nitric acid condensing column 3. Specifically, the pipe 21 was connected to a location in the nitric acid condensing column 3 that was on the lower side (the lower part of the nitric acid condensing column 3) of the loading location of the packing material. Therefore, the reaction liquid from the reactor 2 was continuously supplied to the lower part of the nitric acid condensing column 3. A distillation process was carried out in the same manner as in Example 1 except for the facts that the pressure of the nitric acid condensing column 3 was set to 100 Toor (approximately 13 kPa), the flow rate of the reaction liquid supplied to the nitric acid condensing column 3 from the reactor 2 was set to 200.2 g/h, and the extraction amount of the condensed liquid from the nitric acid condensing column 3 was set to 20.0 g/h in addition to the above-described change. The results of Example 4 are summarized in Table 1.

The temperature at the bottom part of the nitric acid condensing column 3 was 51° C., and the compositions of the distillate liquid and the condensed liquid were as described below. The concentration of methyl nitrate in the distillate liquid was 2 ppm by weight.

The composition of the distillate liquid: 33.8% by weight of methanol, 60.2% by weight of water, and 6.0% by weight of others The composition of the condensed liquid: 3.6% by weight of methanol, 16.0% by weight of nitric acid, 75.0% by weight of water, and 5.4% by weight of others Example 5

A distillation process was carried out in the same manner as in Example 1 except for the facts that, similar to Example 4, the reaction liquid was continuously supplied to the lower part of the nitric acid condensing column 3, the flow rate of the reaction liquid supplied to the nitric acid condensing column 3 from the reactor 2 was set to 199.9 g/h, and the extraction amount of the condensed liquid from the nitric acid condensing column 3 was set to 32.0 g/h. The results of Example 5 are summarized in Table 1.

The temperature at the bottom part of the nitric acid condensing column 3 was 76° C., and the compositions of the distillate liquid and the condensed liquid were as described below. The concentration of methyl nitrate in the distillate liquid was 13 ppm by weight.

The composition of the distillate liquid: 36.1% by weight of methanol, 57.6% by weight of water, and 6.3% by weight of others The composition of the condensed liquid: 2.9% by weight of methanol, 10.0% by weight of nitric acid, 83.0% by weight of water, and 4.1% by weight of others Comparative Example 1

A distillation process was carried out in the same manner as in Example 5 except for the facts that the flow rate of the reaction liquid supplied to the nitric acid condensing column 3 from the reactor 2 was set to 201.0 g/h, and the extraction amount of the condensed liquid from the nitric acid condensing column 3 was set to 20.1 g/h. The results of Comparative Example 1 are summarized in Table 1.

The temperature at the bottom part of the nitric acid condensing column was 78° C., and the compositions of the distillate liquid and the condensed liquid were as described below. The concentration of methyl nitrate in the distillate liquid was 500 ppm by weight.

The composition of the distillate liquid: 33.8% by weight of methanol, 60.2% by weight of water, and 6.0% by weight of others The composition of the condensed liquid: 4.0% by weight of methanol, 16.0% by weight of nitric acid, 75.0% by weight of water, and 5.0% by weight of others Comparative Example 2

A distillation process was carried out in the same manner as in Example 5 except for the facts that the pressure in the nitric acid condensing column 3 was set to normal pressure, the flow rate of the reaction liquid supplied to the nitric acid condensing column 3 from the reactor 2 was set to 199.5 g/h, and the extraction amount of the condensed liquid from the nitric acid condensing column 3 was set to 31.9 g/h. The results of Comparative Example 2 are summarized in Table 1.

The temperature at the bottom part of the nitric acid condensing column was 98° C., and the compositions of the distillate liquid and the condensed liquid were as described below. The concentration of methyl nitrate in the distillate liquid was 150 ppm by weight.

The composition of the distillate liquid: 35.5% by weight of methanol, 58.2% by weight of water, and 6.3% by weight of others The composition of the condensed liquid: 6.2% by weight of methanol, 10.0% by weight of nitric acid, 80.0% by weight of water, and 3.8% by weight of others

TABLE 1

|  | Example 1 | Example 2 | Example 3 | Example 4 | Example 5 | Comparative Example 1 | Comparative Example 2 |
|---|---|---|---|---|---|---|---|
| Concentration of methanol in condensed liquid [% by weight] | 0.006 | 0.105 | 0.9 | 3.6 | 2.9 | 4.0 | 6.2 |
| Supply location to nitric acid condensing column 3 | Upper part | Upper part | Upper part | Lower part | Lower part | Lower part | Lower part |
| Pressure in nitric acid condensing column 3 [Torr] | 300 | 300 | 300 | 100 | 300 | 300 | Normal pressure |
| Number of packing material [pieces] | 5 | 5 | 1 | 5 | 5 | 5 | 5 |
| Concentration of nitric acid in condensed liquid [% by weight] | 10.7 | 18 | 18 | 16 | 10 | 16 | 10 |
| Concentration of methyl nitrate in distillate liquid [ppm by weight] | 0.2 | 0.6 | 8 | 2 | 13 | 500 | 150 |
| Temperature at bottom part of nitric acid condensing column 3 [° C.] | 78 | 80 | 81 | 51 | 76 | 78 | 98 |

In Examples 1 to 5 in which the concentrations of methanol in the condensed liquids were controlled to less than 4.0% by weight, it is found that the concentrations of methyl nitrate in the distillate liquids were sufficiently low, and the losses of the nitrogen components were small. In addition, when Examples 1 and 5 are compared, it is found that, in a case in which the reaction liquid was supplied to the upper part of the nitric acid condensing column, the concentration of methyl nitrate in the distillate liquid became low compared with a case in which the reaction liquid was supplied to the lower part. Furthermore, when Examples 1 and 3 are compared, it is found that the concentration of methyl nitrate in the distillate liquid became lower in Example 1 in which the number of theoretical stages was approximately five than in Example 3 in which the number of theoretical stages was approximately one.

INDUSTRIAL APPLICABILITY

According to the invention, it is possible to provide a method for producing nitrous acid ester capable of decreasing the loss of a nitrogen component by sufficiently reducing the concentration of nitric acid in a liquid waste. The method for producing nitrous acid ester can be preferably used when a dialkyl oxalate and a dialkyl carbonate are produced.

REFERENCE SIGNS LIST

1 . . . REACTION COLUMN FOR PRODUCING NITROUS ACID ESTER, 2 . . . REACTOR FOR NITRIC ACID CONVERSION, 3 . . . NITRIC ACID CONDENSING COLUMN, 4 . . . COOLER, 5 . . . REACTOR FOR PRODUCING OXALATE DIESTER AND/OR CARBONATE DIESTER, 6 . . . ABSORPTION COLUMN, 11 . . . ALCOHOL SUPPLY LINE, 12 . . . RAW MATERIAL GAS SUPPLY LINE, 13 . . . FIRST REACTION GAS EXTRACTION LINE, 14 . . . BOTTOM LIQUID EXTRACTION LINE, 15 . . . OXYGEN SUPPLY LINE, 16 . . . CARBON MONOXIDE SUPPLY LINE, 17 . . . NITRIC OXIDE SUPPLY LINE, 18, 31 . . . SECOND REACTION GAS EXTRACTION LINE, 19 . . . BOTTOM LIQUID CIRCULATION LINE, 20 . . . PURGE LINE, 21, 32 . . . CARBON MONOXIDE SUPPLY LINE, 22 . . . CONDENSED LIQUID EXTRACTION LINE, 23 . . . CONDENSED LIQUID CIRCULATION LINE, 24 . . . DISTILLATE LIQUID EXTRACTION LINE, 25 . . . LIQUID WASTE EXTRACTION LINE, 26 . . . THIRD REACTION GAS EXTRACTION LINE, 27 . . . ABSORPTION LIQUID SUPPLY LINE, 28 . . . CONDENSATE LIQUID EXTRACTION LINE, 100, 101, 102 . . . APPARATUS FOR PRODUCING NITROUS ACID ESTER, 200, 201 . . . PRODUCING APPARATUS

The invention claimed is:

1. A method for producing nitrous acid ester in which an alcohol is supplied to an upper part of a reaction column for producing nitrous acid ester, is made to flow downward from the upper part to a lower part of the reaction column, nitric oxide and oxygen, or a gas mixture thereof is supplied to the lower part of the reaction column, and nitric oxide, oxygen, and the alcohol are reacted, thereby generating nitrous acid ester, the method comprising:
    a step of extracting a bottom liquid containing water, nitric acid, and an alcohol from the bottom part of the reaction column so as to supply the bottom liquid to a reactor, and supplying nitric oxide and/or carbon monoxide to the reactor;
    a step of generating nitrous acid ester by brining nitric oxide and/or carbon monoxide into contact with the bottom liquid in the reactor;
    a step of supplying nitrous acid ester obtained in the reactor to the reaction column;
    a step of supplying a reaction liquid containing water, nitric acid, and the alcohol to a nitric acid condensing column from a lower part of the reactor; and
    a step of separating a low-boiling point component by distillation from the reaction liquid in the nitric acid condensing column under control of a concentration of an alcohol in a condensed liquid being generated at a bottom part of the nitric acid condensing column to be less than 4.0% by weight, and extracting the condensed liquid from the lower part of the nitric acid condensing column so as to introduce the condensed liquid into the reactor.

2. The method for producing nitrous acid ester according to claim 1,
    wherein the nitrous acid ester obtained in the reactor is supplied to the reaction column from a supply opening provided at a middle part, a lower part, or a part between the middle part and the lower part of the reaction column.

3. The method for producing nitrous acid ester according to claim 1,
    wherein the bottom liquid extracted from the lower part of the reaction column is introduced into and cooled in a cooler, and the bottom liquid which is cooled is circulated to the middle part of the reaction column.

4. The method for producing nitrous acid ester according to claim 1,
    wherein a pressure in the nitric acid condensing column is lower than an atmospheric pressure.

5. The method for producing nitrous acid ester according to claim 1,
    wherein the reaction liquid is supplied to the nitric acid condensing column from a supply opening provided at above a middle part of the nitric acid condensing column.

6. The method for producing nitrous acid ester according to claim 1,
    wherein an alcohol obtained by purifying the low-boiling point component separated by distillation in the nitric acid condensing column is supplied to the reaction column from a supply opening provided at above a middle part of the reaction column.

7. The method for producing nitrous acid ester according to claim 1,
    wherein a temperature of the nitric acid condensing column in a bottom part is 90° C. or lower.

8. The method for producing nitrous acid ester according to claim 1,
    wherein a gas containing carbon monoxide is supplied to the reactor, and the carbon monoxide and the reaction liquid are brought into contact with each other in the reactor in the presence of a platinum group catalyst.

9. A method for producing a dialkyl oxalate, comprising a step of producing a nitrous acid ester according to method of claim 1; and:
    a step of producing a dialkyl oxalate by reacting the nitrous acid ester and carbon monoxide in the presence of a catalyst.

10. A method for producing a dialkyl carbonate, comprising a step of producing a nitrous acid ester according to method of claim 1; and:
    a step of producing a dialkyl carbonate by reacting the nitrous acid ester and carbon monoxide in the presence of a catalyst.

* * * * *